United States Patent [19]

Pretzer et al.

[11] 4,133,966

[45] Jan. 9, 1979

[54] SELECTIVE FORMATION OF ETHANOL FROM METHANOL, HYDROGEN AND CARBON MONOXIDE

[75] Inventors: Wayne R. Pretzer, Oakmont Borough; Thaddeus P. Kobylinski, Gibsonia; John E. Bozik, Plum Borough, all of Pa.

[73] Assignee: Gulf Research & Development Company, Pittsburgh, Pa.

[21] Appl. No.: 863,792

[22] Filed: Dec. 23, 1977

[51] Int. Cl.$^2$ .............................................. C07C 29/00
[52] U.S. Cl. ................................... 568/902; 560/265; 568/671
[58] Field of Search .......................... 260/642; 568/902

[56] References Cited

U.S. PATENT DOCUMENTS

| | | | |
|---|---|---|---|
| 3,248,432 | 4/1966 | Riley et al. | 260/642 B |
| 3,285,948 | 11/1966 | Putter | 260/642 B |
| 3,488,296 | 1/1970 | Senn et al. | 260/632 HF |

*Primary Examiner*—Joseph E. Evans

[57] ABSTRACT

A process for the selective formation of ethanol which comprises contacting methanol, hydrogen and carbon monoxide with a catalyst system comprising cobalt acetylacetonate, a tertiary organo Group V A compound of the periodic Table, a first promoter comprising an iodine compound and a second promoter comprising a ruthenium compound.

23 Claims, No Drawings

SELECTIVE FORMATION OF ETHANOL FROM METHANOL, HYDROGEN AND CARBON MONOXIDE

BACKGROUND OF THE INVENTION

1. Field of the Invention

Ethanol is a compound which has been used by man since time immemorial. Historically, ethanol has been produced for various purposes by the fermentation of common grains. However, within this alcohol for industrial use. Such synthetic processes permit the use of more economical starting materials than those used in the fermentation processes, and additionally, permit production and reproduction of a more standardized product and more easily predictable yields of end product. Methanol can easily and economically be produced in great quantities from hydrogen and carbon monoxide or from almost anything containing carbon and hydrogen, for example, from methane to manure and from coal to crude oil residues. One such process for producing ethanol synthetically involves reacting methanol with carbon monoxide and hydrogen at elevated temperatures and pressures in the presence of a catalyst system.

The conversion of an alcohol, for example, methanol, to the primary alcohol containing one carbon atom more than the original alcohol, namely ethanol, is normally a tedious and time consuming procedure involving a series of steps. Additionally, catalysts which possess acceptable activity generally tend to give a wide spectrum of products, in addition to ethanol, for example, hydrocarbons and oxygenated hydrocarbons having a broad distribution of carbon atoms. This not only complicates the separation and recovery of desired products, but results in reduced yield of ethanol and erosion of reactants in the production of undesirable by-products.

2. Description of the Prior Art

The reaction of methanol with hydrogen and carbon monoxide to produce ethanol is appreciated and disclosed by the prior art. However, in general, most known processes produce an undesirably large mixture of alcohols, aldehydes, ketones and carboxylic acids in addition to the desired alcohol.

For example, U.S. Pat. No. 3,285,948, entitled HALIDES OF RUTHENIUM AND OSMIUM IN CONJUNCTION WITH COBALT AND IODINE IN THE PRODUCTION OF ETHANOL FROM METHANOL, issued to Butter on November 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, $I_2$, or alkali metal iodines. A secondary promoter is also employed, i.e., ruthenium halide or osmium halide. High selectivity is described as better when the secondary promoter is used in combination with the primary promoter and other reactants.

U.S. Pat. No. 4,013,700, entitled CATALYTIC PROCESS FOR POLYHYDRIC ALCOHOLS AND DERIVATIVES, issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled PROCESS FOR THE PRODUCTION OF ETHYL ALCOHOL, issued to Riley et al on Apr. 26, 1966, which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled PREPARATION OF ORGANIC HYDROXY-CONTAINING COMPOUNDS BY REACTING ALCOHOLS WITH CARBON MONOXIDE AND HYDROGEN, issued to Greshaw on June 16, 1948, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts. The process, however, suffers from the disadvantage of poor product distribution.

Dutch Pat. No. 760,6138 entitled PROCESS FOR THE FORMATION OF ETHANOL FROM METHANOL AND SYNTHESIS GAS, issued to Shell International Research on June 8, 1976, relates to a process for producing alcohols which utilizes any soluble cobalt source which can generate a cobalt carbonyl or hydro carbonyl by reaction with the synthesis gas. For example, sources of cobalt suitable for use are cobalt iodide or cobalt metal from which ions can be generated in situ. Organic salts of cobalt such as cobalt acetate, formate, or propionate are described as especially good sources, an iodide or bromide promoter is also utilized. In addition, the use of a tertiary phosphine is described as affording improved selectivity to the formation of alcohols.

Unexpectedly, we have discovered that not all cobalt and ruthenium sources give similar results that is, produce a product containing a large amount of ethanol with a minimum amount of other products. Generally, catalysts which possess excellent activity, generally, tend to give a wide spectrum of products, for example, hydrocarbons and oxygenated hydrocarbons having a product distribution of varying carbon atom content. This not only complicates the recovery of desired products, but results in the wastage of reactants to commercially uninteresting by-products.

SUMMARY OF THE INVENTION

The present invention relates to a process for the selective homologation of methanol to ethanol wherein methanol is reacted with hydrogen and carbon monoxide in the presence of a catalyst, the improvement which comprises contacting methanol, hydrogen and carbon monoxide with cobalt acetylacetonate, a tertiary organo Group V A compound of the Periodic Table of the formula:

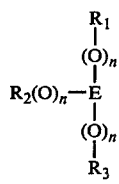

wherein E is a member selected from the group consisting of trivalent phosphorus, trivalent arsenic and trivalent antimony; and $R_1$, $R_2$ and $R_3$ are either alike or different members selected from the group consisting of saturated or unsaturated, straight or branched chain alkyl radicals having from about 1 to about 24 carbon atoms, preferably from about 1 to about 10 carbon atoms; aryl radicals having from about 6 to about 20 carbon atoms, preferably from about 6 to about 10 carbon atoms; alkenyl radicals having from about 1 to about 30 carbon atoms, preferably from about 1 to about 20 carbon atoms; cycloalkyl radicals having from about 3 to about 40 carbon atoms, preferably from about 3 to about 30 carbon atoms; aralkyl and alkaryl radicals having from about 6 to about 40 carbon atoms, preferably from about 6 to about 30 carbon atoms; and n is an integer of 0 or 1 with the provision that when n is 1, E must be phosphorus; an iodine promoter and as a second promoter a ruthenium compound.

DESCRIPTION OF THE INVENTION

The present invention resides in a process for the homologation of methanol to ethanol which comprises contacting methanol, hydrogen and carbon monoxide with cobalt acetylacetonate, a tertiary organo Group V A compound of the periodic table, an iodine promoter and as a second promoter a ruthenium compound under reaction conditions for a time period sufficient to produce said ethanol. Although hydrogen and carbon monoxide are employed herein for reaction with methanol to produce ethanol, it is understood that any combination of compounds that will form hydrogen and carbon monoxide in the reaction zone can also be used, for example, mixtures of hydrogen and carbon dioxide, water and carbon monoxide, etc.

The mixture of hydrogen and carbon monoxide used herein can be produced from anything containing carbon and hydrogen. Two types of reactions, for example, can be used for the production of synthesis gas, partial oxidation and steam reforming. Steam reforming is the more important process when natural gas (methane) is the hydrogen-carbon source. Partial oxidation is used primarily for heavy fuel and residue.

The relative amounts of hydrogen and carbon monoxide present in the reaction mixture can be varied over a wide range. However, in general, the molar ratio range of hydrogen to carbon monoxide is from about 10:1 to about 1:10, especially from about 3:1 to about 1:3; however, conventional synthesis gas (mixtures of hydrogen and carbon monoxide) with a molar ratio of about 1:1 is convenient and satisfactory for the process herein. It is to be noted that molar ratios outside the aforestated ratio ranges can be employed herein and as pointed out hereinabove compounds or reaction mixtures which give rise to the formation of carbon monoxide and hydrogen under the reaction conditions defined herein can be used instead of mixtures comprising hydrogen and carbon monoxide which are used in the preferred embodiments of this invention.

In a preferred mode, methanol, hydrogen and carbon monoxide are introduced into a pressure resistant reaction vessel, for example, a stainless steel autoclave with agitation means. Agitation is defined herein as shaking, rocking, stirring, percolation with synthesis gas, etc. Methanol can be converted into ethanol in a batch operation or in a continuous process. When the batch method is used, methanol, hydrogen and carbon monoxide, cobalt acetylacetonate, a tertiary organo Group V A compound of the periodic table, iodine promoter and a ruthenium compound are introduced into the reaction vessel and the pressure and temperature are adjusted to the operating reaction conditions. If the system is a closed system, the pressure is raised to the desired level with hydrogen and carbon monoxide before the reaction is initiated and the pressure falls as the reaction proceeds, but never below reaction pressure. Alternatively, the system can be equipped with a reservoir which contains synthesis gas and which feeds said gas to the reaction vessel at a set pressure on demand, thus maintaining a particular pressure level.

In a continuous process for producing ethanol, methanol, hydrogen and carbon monoxide, cobalt acetylacetonate, a tertiary organo Group V A compound of the periodic table, an iodine promoter and a ruthenium compound are continuously fed into a pressure resistant reaction vessel as described herein at a constant rate. The cobalt acetylacetonate and promoters are normally dissolved in an inert solvent, for example, ethylene, glycol, 1,2-dimethyl ethane, or acetone, before introduction into the reaction vessel for ease of application and recovery of the cobalt compound and promoters. The mixture of methanol, synthesis gas, cobalt acetylacetonate, a tertiary organo Group V A compound of the periodic table, iodine promoter and ruthenium compound is next reacted under reaction conditions for a time period sufficient to convert methanol to ethanol.

Pressures which are suitable for use in our process, for example, generally are above about 1000 psig (6.83 MPA), but should not be in excess of about 10,000 psig (68.30 MPA). An especially desirable pressure range is from about 1000 psig (6.83 MPA) to about 6000 psig (40.98 MPA), preferably from about 2000 psig (13.66 MPA) to about 5000 psig (34.15 MPA). Temperatures which are suitable for use in our process are those temperatures which initiate a reaction between the reactants herein to produce ethanol, generally from about 150° C. to about 250° C., preferably from about 175° C. to about 225° C. The reaction is conducted for a time period sufficient to convert methanol to ethanol, normally from about 0.5 hour to about 10 hours, especially from about 1 hour to about 5 hours.

Recovery of the desired ethanol from the reaction product can be effected in any convenient or conventional manner, for example, by distillation. At ambient pressure and about 21° C., the components will distill off in the following sequence for the desired recovery: dimethyl ether, diethyl ether, methyl acetate, methanol and ethanol.

It is to be noted that the catalyst system herein is highly selective to the formation of ethanol and minimizes the formation of undesirable by-products such as acetaldehyde, ethers, esters and other alcohol derivatives.

Any soluble source of cobalt can be used to produce ethanol from the above reactants, namely, methanol, hydrogen and carbon monoxide. However, most cobalt sources have the disadvantage of producing a wide variety of alcohols and their derivatives from the above reactants and do not optimize the formation of ethanol. Generally, the molar concentration of cobalt acetylacetonate to methanol is from about 1:1 to about 1:100,000, especially from about 1:1 to about 1:2,000.

Tertiary organo Group V A compounds of the periodic table which are suitable for use as ligands herein are of the formula:

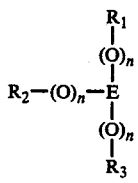

wherein E is a member selected from the group consisting of trivalent phosphorus, trivalent arsenic and trivalent antimony; and $R_1$, $R_2$ and $R_3$ are either alike or different members selected from the group consisting of saturated or unsaturated, straight or branched chain alkyl radicals having from about 1 to about 24 carbon atoms, preferably from about 1 to about 10 carbon atoms; aryl radicals having from about 6 to about 20 carbon atoms, preferably from about 6 to about 10 carbon atoms; alkenyl radicals having from about 1 to about 30 carbon atoms, preferably from about 1 to about 20 carbon atoms; cycloalkyl radicals having from about 3 to about 40 carbon atoms, preferably from about 3 to about 30 carbon atoms; aralkyl and alkaryl radicals having from about 6 to about 50 carbon atoms, preferably from about 6 to about 30 carbon atoms; and n is an integer of 0 or 1 with the provision that when n is 1, E must be phosphorus Tertiary organo Group V A compounds which are suitable for use herein include:
tri-methyl-phosphite
tri-ethyl-phosphine
tri-n-butyl-phosphine
tri-isopropyl-phosphine
tri-cyclo-hexyl-phosphite
tri-cyclo-hexyl-phosphine
tri-cyclo-heptyl-phosphine
di-phenyl-methyl-phosphine
tri-phenyl-phosphine
tri-naphthyl-phosphine
tri-styryl-phosphine
vinyl-diphenyl-phosphine
tri-benzyl-phosphite
tri-benzyl-phosphine
tri-para-tolyl-phosphite
tri-para-tolyl-phosphine
tri-ethyl-arsine
tri-n-butyl-arsine
tri-isopropyl-arsine
tri-cyclo-hexyl-arsine
tri-cyclo-heptyl-arsine
di-phenyl-methyl-arsine
tri-phenyl-arsine
tri-naphthyl-arsine
tri-styryl-arsine
vinyl-diphenyl-arsine
tri-benzyl-arsine
tri-para-tolyl-arsine
tri-ethyl-antimony
tri-n-butyl-antimony
tri-isopropyl-antimony
tri-cyclo-hexyl-antimony
tri-cyclo-heptyl-antimony
di-phenyl-methyl-antimony
tri-phenyl-antimony
tri-naphthyl-antimony
tri-styryl-antimony
vinyl-diphenyl-antimony
tri-benzyl-antimony, and
tri-para-tolyl-antimony, or mixtures thereof. It should be noted that the tertiary organo group V A compounds herein are superior in the combined selectivity to formation of $C_2$ products, including ethanol. Normally, the cobalt acetylacetonate and the tertiary organo Group V A compound used are in a molar ratio of from about 1:20 to about 20:1 especially from about 1:1 to about 6:1.

Any source of iodine which is capable of disassociating that is, ionizing to form free iodine ions, in the reaction medium can be used as a primary promoter in the present invention. Illustrative examples of iodine promoters especially suitable for use are preferably members selected from the group consisting of iodine, potassium iodide, calcium iodide, sodium iodide, lithium iodide, hydrogen iodide, methyl iodide, ethyl iodide, and the like. Normally, the cobalt acetylacetonate and the iodine promoter herein are mixed in a molar ratio range of from about 1:100 to about 100:1, preferably from about 1:10 to about 10:1, respectively.

The second promoter of the present invention is preferably a ruthenium compound, and is employed in the reaction medium under reaction conditions in catalytically effective amounts. Preferably, the cobalt acetylacetonate and ruthenium compound are used in a molar ratio of from about 1:20 to about 20:1, especially from about 3:0.19 to about 3:1.5, preferably from about 3:0.19 to about 3:0.75. It should be noted that the cobalt acetylacetonate, tertiary organo Group V A compound, iodine promoter and ruthenium compound combination herein, is highly selective to ethanol formation when contacted with methanol, hydrogen and carbon monoxide under reaction conditions. It should additionally be noted that when the above molar ratio of cobalt acetylacetonate to tertiary organo Group V A compound is above about 3:1.5 or below about 3:0.19, the reaction is still selective to the formation of ethanol, however, lower yields of ethanol are obtained.

Ruthenium compounds which are suitable for use herein include: ruthenium acetylacetonate, ruthenium trichloride, ruthenium tribromide, ruthenium triiodide, ruthenium acetate, ruthenium propionate, ruthenium octonate, ruthenium dioxide, ruthenium tetraoxide, ruthenium pentacarbonyl and tri-ruthenium dodecacarbonyl.

DESCRIPTION OF PREFERRED EMBODIMENTS

The following Examples and Table serve to further illustrate and instruct one skilled in the art the best mode of how to practice this invention and are not intended to be construed as limiting thereof.

The reactions herein were performed in a stainless steel pressure-resistant autoclave equipped with agitation means, for example, a type 316 stainless steel, 300 cc autoclave marketed commercially by Autoclave Engineers. The methanol, hydrogen, carbon monoxide, cobalt acetylacetonate, and iodine promoter and ruthenium compound were introduced into the autoclave. The autocalve was connected to another larger reservoir containing synthesis gas (hydrogen and carbon monoxide) which fed said synthesis gas into the steel autoclave at a set pressure on demand. Thus, the reactor pressure was maintained throughout the course of the reaction. The reaction pressure and temperature were adjusted to operating conditions and the mixture reacted for a period of time sufficient to produce ethanol.

EXAMPLES I - VII

Into a 300 cc stainless steel autoclave were charged 3 millimoles of cobalt acetylacetonate, 0.75 millimole of iodine, 0.5 millimole of a tertiary organo Group V A compound, 0.75 millimole of ruthenium compound, and 100 millimoles of methanol (see Table I). The reactor was next purged twice with nitrogen gas and then pressurized with synthesis gas ($H_2$:$CO$=1) to a pressure of about 1000 psig (6.83 MPA) lower than the desired working pressure. The system was then heated to a temperature of about 175° C., and the pressure was adjusted to a working pressure of about 4000 psig (27.6 MPA). The reaction was allowed to proceed for approximately three hours, after which the reactor was cooled by an internal cooling coil to about −75° C. The reactor was vented through a dry gas meter and a gas sample was taken for a mass spectral analysis, and the liquid product was analyzed using a Model 900 Perkin-Elmer gas chromatograph utilizing a 16 ft. (4.88 meters) × 1.8 in. (0.32 centimeter) stainless steel column wherein 8 ft. (2.44 meters) of the column was packed with 80/100 mesh Poropak Q and the other 8 ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min and with a helium blow rate of 30 cc/min. The above procedure was followed in the Examples set forth in Table I below.

A compound, iodine promoter and ruthenium compound catalyst system herein is highly selective to the formation of ethanol from methanol, hydrogen and carbon monoxide. It should additionally be noted that higher temperatures will give a higher conversion rate for methanol. In general, however, temperatures above about 250° C. tend to favor the formation of ethers, esters, etc. and should be avoided. Any of the other tri-organo Group V A compounds, iodine promoters and ruthenium compounds herein may be substituted for the corresponding compounds in the above Examples with substantially the same results.

EXAMPLE VIII

The procedure of Example I is followed with the following exception: tri-ethyl-arsine is the tri-organo Group V A compound; sodium iodide is the iodine compound and ruthenium acetate is the ruthenium compound. Substantially the same results are obtained with excellent selectivity to ethanol formation. Any of the trivalent arsenic compounds disclosed herein can be substituted for tri-ethyl-arsine above.

EXAMPLE IX

The procedure set forth in Example I is followed with the following substitutions: tri-phenyl-antimony is the tri-organo Group V A compound; potassium iodide is the iodine compound and ruthenium propionate is the ruthenium compound. The above catalyst system is highly selective to ethanol formation. It is to be noted that the other trivalent antimony compounds herein can be substituted for the tri-phenyl-antimony above with substantially the same results.

EXAMPLE X

A 300 cc stainless steel autoclave is charged with 3 millimoles of cobalt acetylacetonate, 0.75 millimole of iodine, 0.5 millimole of tri-cyclo-hexyl-phosphine, 0.76 millimole of ruthenium acetylacetonate, and 100 milli-

TABLE I

| Example No. | Catalyst System | Co/Ru Molar Ratio | % MeOH[a] Conv. | Mole % Selectivity | | | | |
|---|---|---|---|---|---|---|---|---|
| | | | | $Me_2O$[b] | AcH[c] | EtOH[d] | MeOAc[e] | $Et_2O$[f] |
| I | Cobalt Acetylacetonate + tri-para-tolyl-phosphite + iodine + ruthenium acetylacetonate | 3:0.75 | 59.0 | 4.6 | — | 59.8 | 14.9 | 14.0 |
| II | Cobalt acetylacetonate + tri-para-tolyl-phosphite + iodine + ruthenium dioxide | 3:0.75 | 39.4 | 7.0 | — | 56.7 | 18.8 | 13.8 |
| III | Cobalt acetylacetonate + tri-para-tolyl-phosphite + iodine + ruthenium tri-chloride | 3:0.75 | 39.6 | 6.8 | — | 54.4 | 18.7 | 14.5 |
| IV | Cobalt acetylacetonate + tri-para-tolyl-phosphite + iodine + tri-ruthenium dodecacarbonyl | 3:0.75 | 38.3 | 10.4 | — | 49.4 | 15.2 | 17.5 |
| V | Cobalt acetylacetonate + tri-n-butyl-phosphine + iodine + ruthenium acetylacetonate | 3:0.75 | 42.1 | 7.6 | — | 53.9 | 18.8 | 15.2 |
| VI | Cobalt acetylacetonate + tri-phenyl phosphine + iodine + ruthenium acetylacetonate | 3:0.75 | 48.1 | 7.0 | — | 58.2 | 18.4 | 13.4 |
| VII | Cobalt acetylacetonate + tri-isopropyl-phosphite + iodine + ruthenium acetylacetonate | 3:0.75 | 49.0 | 7.0 | — | 58.2 | 18.1 | 12.2 |

[a] MeOH = Methanol
[b] $Me_2O$ = Dimethyl ether
[c] AcH = Acetaldehyde
[d] EtOH = Ethanol
[e] MeOAc = Methyl acetate
[f] $Et_2O$ = Diethyl ether
Cobalt acetylacetonate/iodine (molar ratio) = 2:1
Cobalt acetylacetonate/tri organo Group V A Compound (molar ratio) = 6:1
Temperature = 175° C.
Pressure = 4000 psig (27.6 MPA)

As can be determined from the results in Table I above, the cobalt acetylacetonate, tri-organo Group V moles of methanol. The reactor is purged twice with nitrogen gas and pressurized with synthesis gas (H$_2$:Co=1) to a pressure of about 1000 psig (6.83 MPA) lower than the desired working pressure. The system is next heated to a temperature of about 200° C., and the pressure was adjusted to a working pressure of about 4000 psig (27.6 MPA). The reaction is allowed to proceed for approximately three hours. The above catalyst system is highly selective to ethanol formation from reaction of methanol with hydrogen and carbon monoxide.

EXAMPLE XI

The procedure of Example X is followed with the following exception: tri-styryl-phosphine is substituted for the tri-cyclohexyl-phosphine. Substantially the same results are obtained with high selectivity of ethanol formation.

Obviously, many modifications and variations of the invention, as hereinabove set forth, can be made without departing from the spirit and scope thereof, and therefore only such limitations should be imposed as are indicated in the appended claims.

We claim:

1. In a process for the homologation of methanol to ethanol wherein methanol is reacted with hydrogen and carbon monoxide in the presence of a catalyst at a reaction temperature of from about 150° C. to about 250° C. and a reaction pressure of from about 1000 psig (6.83 MPA) to about 6000 psig (40.98 MPA), the improvement which comprises contacting methanol, hydrogen and carbon monoxide with cobalt acetylacetonate, a tertiary organo Group V A compound of the periodic table of the formula:

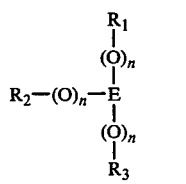

wherein E is a member selected from the group consisting of trivalent phosphorus, trivalent arsenic and trivalent antimony; and R$_1$, R$_2$, and R$_3$ are either alike or different members selected from the group consisting of saturated or unsaturated, straight or branched chain alkyl radicals having from about 1 to about 24 carbon atoms; aryl radicals having from about 6 to about 20 carbon atoms; alkenyl radicals having from about 1 to about 30 carbon atoms; cycloalkyl radicals having from about 3 to about 40 carbon atoms; aralkyl and alkaryl radicals having from about 6 to about 40 carbon atoms; and n is an integer of 0 or 1 with the provision that when n is 1, E must be phosphorus; an iodine promoter, and as a second promoter a ruthenium compound, said cobalt acetylacetonate and said tertiary organo Group V A compound being in a molar ratio of from about 1:20 to about 20:1, said cobalt acetylacetonate and said iodine promoter being in a molar ratio of from about 1:100 to about 100:1 and said cobalt acetylacetonate and said ruthenium compound being in a molar ratio of from about 1:20 to about 20:1.

2. The process of claim 1 wherein R$_1$, R$_2$ and R$_3$ are either alike or different members selected from the group consisting of alkyl radicals having from about 1 to about 10 carbon atoms; aryl radicals having from about 6 to about 10 carbon atoms; alkenyl radicals having from about 1 to about 20 carbon atoms; cycloalkyl radicals having from about 3 to about 30 carbon atoms; aralkyl and alkaryl radicals having from about 6 to about 30 carbon atoms.

3. The process of claim 1 wherein the tertiary organo Group V A compound is a member selected from the group consisting of:
tri-methyl-phosphite
tri-ethyl-phosphine
tri-n-butyl-phosphine
tri-isopropyl-phosphine
tri-cyclo-hexyl-phosphite
tri-cyclo-hexyl-phosphine
tri-cyclo-heptyl-phosphine
di-phenyl-methyl-phosphine
tri-phenyl-phosphine
tri-naphthyl-phosphine
tri-styryl-phosphine
vinyl-diphenyl-phosphine
tri-benzyl-phosphite
tri-benzyl-phosphine
tri-para-tolyl-phosphite
tri-para-tolyl-phosphine
tri-ethyl-arsine
tri-n-butyl-arsine
tri-isopropyl-arsine
tri-cyclo-hexyl-arsine
tri-cyclo-heptyl-arsine
di-phenyl-methyl-arsine
tri-phenyl-arsine
tri-naphthyl-arsine
tri-styryl-arsine
vinyl-diphenyl-arsine
tri-benzyl-arsine
tri-para-tolyl-arsine
tri-ethyl-antimony
tri-n-butyl-antimony
tri-isopropyl-antimony
tri-cyclo-hexyl-antimony
tri-cyclo-heptyl-antimony
di-phenyl-methyl-antimony
tri-phenyl-antimony
tri-naphthyl-antimony
tri-styryl-antimony
vinyl-diphenyl-antimony
tri-benzyl-antimony, and
tri-para-tolyl-antimony, or mixtures thereof.

4. The process of claim 1 wherein the tertiary organo Group V A compound is tri-para-tolyl-phosphite.

5. The process of claim 1 wherein the tertiary organo Group V A compound is tri-n-butyl-phosphine.

6. The process of claim 1 wherein the tertiary organo Group V A compound is tri-phenyl-phosphine.

7. The process of claim 1 wherein the tertiary organo Group V A compound is tri-isopropyl phosphite.

8. The process of claim 1 wherein the cobalt acetylacetonate and methanol are in a molar ratio of from about 1:1 to about 1:100,000.

9. The process of claim 1 wherein cobalt acetylacetonate and methanol are in a molar ratio of from about 1:1 to about 1:2,000.

10. The process according to claim 1 wherein the cobalt acetylacetonate and the tertiary organo Group V A compound are in a molar ratio of from about 1:1 to about 6:1.

11. The process of claim 1 wherein the cobalt acetylacetonate and iodine promoter are in a molar ratio of from about 1:10 to about 10:1.

12. The process of claim 1 wherein the iodine promoter is a member selected from the group consisting of iodine, calcium iodide, sodium iodide, lithium iodide, hydrogen iodide, methyl iodide and ethyl iodide, or mixtures thereof.

13. The process of claim 1 wherein the iodine promoter is iodine.

14. The process of claim 1 wherein the cobalt acetylacetonate and ruthenium compound are in a molar ratio of from about 3:0.19 to about 3:1.5.

15. The process of claim 1 wherein the ruthenium compound is a member selected from the group consisting of: ruthenium acetylacetonate, ruthenium trichloride, ruthenium tribromide, ruthenium dioxide, ruthenium acetate, ruthenium propionate, ruthenium octonate, ruthenium dioxide, ruthenium tetraoxide, ruthenium pentacarbonyl and tri-ruthenium dodecarbonyl, or mixtures thereof.

16. The process of claim 1 wherein the ruthenium compound is ruthenium acetylacetonate.

17. The process of claim 1 wherein the ruthenium compound is ruthenium dioxide.

18. The process of claim 1 wherein the ruthenium compound is ruthenium trichloride.

19. The process of claim 1 wherein the ruthenium compound is tri-ruthenium-dodeca carbonyl.

20. The process of claim 1 having a reaction temperature of from about 175° C. to about 225° C.

21. The process of claim 1 having a reaction pressure of from about 2000 psig (13.66 MPA) to about 5000 psig (34.15 MPA)

22. The process of claim 1 having a time period of from about 0.5 hour to about 10 hours.

23. The process of claim 1 having a time period of from about 1 hour to about 5 hours.

* * * * *

UNITED STATES PATENT OFFICE
CERTIFICATE OF CORRECTION

Patent No. 4,133,966           Dated January 9, 1979

Inventor(s) Wayne R. Pretzer, Thaddeus P. Kobylinski and
            John E. Bozik It is certified that error appears in the above-identified patent and that said Letters Patent are hereby corrected as shown below:

COL. 1, line 11, the following line was deleted:
--recent years synthetic processes have been developed to synthesize--.

Signed and Sealed this

Seventeenth Day of July 1979

[SEAL]

Attest:

LUTRELLE F. PARKER

Attesting Officer       Acting Commissioner of Patents and Trademarks